(12) United States Patent
Shashanka Jain

(10) Patent No.: US 12,377,200 B2
(45) Date of Patent: Aug. 5, 2025

(54) PERITONEAL DIALYSIS USING PRESSURIZED CYLINDER

(71) Applicants: BAXTER INTERNATIONAL INC., Deerfield, IL (US); BAXTER HEALTHCARE SA, Glattpark (CH)

(72) Inventor: Belur Shanthakumar Shashanka Jain, Bangalore (IN)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 443 days.

(21) Appl. No.: 17/927,135

(22) PCT Filed: May 25, 2021

(86) PCT No.: PCT/US2021/034064
§ 371 (c)(1),
(2) Date: Nov. 22, 2022

(87) PCT Pub. No.: WO2021/242764
PCT Pub. Date: Dec. 2, 2021

(65) Prior Publication Data
US 2023/0201435 A1    Jun. 29, 2023

(30) Foreign Application Priority Data
May 27, 2020   (IN) .............................. 202041022214

(51) Int. Cl.
*A61M 1/28* (2006.01)
*A61M 1/14* (2006.01)
(Continued)

(52) U.S. Cl.
CPC ............ *A61M 1/282* (2014.02); *A61M 1/154* (2022.05); *A61M 1/155* (2022.05);
(Continued)

(58) Field of Classification Search
CPC .... A61M 1/1524; A61M 1/154; A61M 1/155; A61M 1/1561; A61M 1/1565;
(Continued)

(56) References Cited

U.S. PATENT DOCUMENTS

| | | |
|---|---|---|
| 6,491,658 B1 | 12/2002 | Hiromu et al. |
| 2019/0321535 A1 | 10/2019 | Beavers et al. |
| 2021/0138139 A1 | 5/2021 | Hedmann et al. |

FOREIGN PATENT DOCUMENTS

| | | |
|---|---|---|
| WO | 2006054720 | 5/2006 |
| WO | 2019007992 | 1/2019 |

OTHER PUBLICATIONS

International Preliminary Report on Patentability and Written Opinion for International application No. PCT/US2021/034064 dated Dec. 8, 2022.

(Continued)

*Primary Examiner* — John Kim
(74) *Attorney, Agent, or Firm* — K&L Gates LLP

(57) ABSTRACT

A peritoneal dialysis system includes a control unit configured to cause (i) a fluid inlet valve and a fluid outlet valve to occlude a fluid inlet line and a fluid outlet line, respectively, while a linear actuator moves a piston to create a positive pressure within a pump housing, the positive pressure measured by a pressure sensor, and (ii) the fluid inlet valve to occlude the fluid inlet line and the fluid outlet valve to open the fluid outlet line, while the linear actuator moves the piston so as to maintain the positive pressure within the pump housing while fluid is pumped out of the fluid pump chamber via the opened fluid outlet line.

22 Claims, 6 Drawing Sheets

(51) Int. Cl.
*A61M 1/16* (2006.01)
*F04B 43/067* (2006.01)

(52) U.S. Cl.
CPC .......... *A61M 1/1565* (2022.05); *A61M 1/159* (2022.05); *A61M 1/1639* (2014.02); *A61M 1/1641* (2014.02); *A61M 1/281* (2014.02); *A61M 1/285* (2013.01); *F04B 43/067* (2013.01); *A61M 1/1524* (2022.05); *A61M 1/1561* (2022.05); *A61M 2205/07* (2013.01); *A61M 2205/3331* (2013.01); *A61M 2205/3351* (2013.01)

(58) Field of Classification Search
CPC .. A61M 1/159; A61M 1/1639; A61M 1/1641; A61M 1/281; A61M 1/282; A61M 1/285; A61M 2205/07; A61M 2205/3331; A61M 2205/3351; F04B 43/067
See application file for complete search history.

(56) References Cited

OTHER PUBLICATIONS

International Search Report—International Application No. PCT/US2021/034064 mailing date Jul. 27, 2021—27 pages.
Written Opinion—International Application No. PCT/US2021/034064 mailing date Jul. 27, 2021—9 pages.

PERITONEAL DIALYSIS USING PRESSURIZED CYLINDER

CROSS REFERENCE TO RELATED APPLICATIONS

The present application is a National Phase of International Application No. PCT/US2021/034064, filed May 25, 2021, which claims priority to and the benefit of Indian application No. 202041022214, filed May 27, 2020, the entire contents of each of which are incorporated herein by reference in their entirety.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue. Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

There is also a need for APD devices to be portable so that a patient may bring his or her device on vacation or for work travel.

For each of the above reasons, it is desirable to provide a relatively simple, compact dialysis machine, such as an APD machine, which operates a simple and cost effective disposable set.

SUMMARY

The present disclosure relates to an automated peritoneal dialysis ("APD") machine or cycler, which uses a relatively simple and inexpensive disposable set that includes a pump chamber and tubing in fluid communication with the pump chamber that extends to different fluid lines of the system. In one embodiment, a common inlet/outlet line extends from the pump chamber and splits into multiple, e.g., five, separate lines. The separate lines may include at least one supply line and a last fill line to carry fresh dialysis fluid from supply and last fill containers, respectively, to the pump chamber before heating. Fresh dialysis fluid from the supply and last fill containers is then pumped from the pump chamber to a heating container for batch heating via a heater line. Heated, fresh dialysis fluid is then pumped from the heating container to the pump chamber via the heater line. Heated, fresh dialysis fluid is then pumped from the pump chamber to the patient through a patient line, after which used dialysis fluid is pumped from the patient through the patient line to the pump chamber. Used dialysis fluid is finally pumped from the pump chamber to drain through a drain line.

In an alternative embodiment, inline heating is provided that heats fresh dialysis fluid flowing through one or more of the fresh dialysis fluid lines and/or the patient line. In another alternative embodiment, the fresh and last fill containers or bags are located within a heater chamber or blanket. In either case, a separate heater line and heating container or bag are not needed.

The pump chamber is in one embodiment circular and made of at least one flexible membrane. A single flexible membrane may be sealed (e.g., heat sealed, ultrasonically sealed, solvent bonded) to a rigid polymer portion of the disposable set or be sealed to another flexible membrane. The common inlet/outlet line of the disposable set in an alternative embodiment splits into an inlet line that runs to an inlet of the pump chamber and an outlet line that extends from an outlet the pump chamber. All components of the disposable set, including all fluid lines, fluid containers and the pump chamber (flexible and rigid if provided) may be made of any one or more plastic, such as, polyvinyl chloride ("PVC"), polyethylene ("PE") or polyurethane ("PU"), or other suitable non-PVC polymer.

The cycler in an embodiment provides a valve, such as an electrically actuated solenoid valve, a motorized pinch valve, or a pneumatically actuated valve, for each fluid line listed above. The valves provide for independent control (open or closed) of each fluid line. The cycler in one embodiment may also provide an inlet valve that operates with an inlet line that may extend from the common inlet/outlet line to the pump chamber and an outlet valve that operates with an outlet line that may extend from the pump chamber to the common inlet/outlet line. The inlet and outlet valves may also be electrically actuated solenoid valves or pneumatically actuated valves. The inlet and outlet valves are alternatively different ones of the fluid valves for the individual fluid lines depending on the current pump sequence, e.g., to the heater, to the patient or to drain.

The cycler also includes a rigid pump housing that seals to and operates with the flexible pump chamber. The rigid pump housing is in pneumatic communication with a cylinder via a pressure sensing line having a pressure sensor. The rigid pump housing and the cylinder may be made of plastic, such as, polyvinyl chloride ("PVC"), polyethylene ("PE") or polyurethane ("PU"), or of metal, such as stainless steel or aluminum, and combinations thereof.

A piston is moved back and forth within the cylinder via a motor operating with an encoder (for knowing position of the piston). The piston is slideably sealed to an inner wall of the cylinder. The motor operates with a lead screw, ball screw of other rotational to translational conversion apparatus to produce translational motion of the piston within the cylinder. A different type of linear actuator and location determining mechanism may be used alternatively.

All valves, the motor (or other linear actuator), and the fluid heater are under control of a control unit, which includes at least one processor, at least one memory and a video controller for controlling a user interface. The control unit is further configured to receive signals from all sensors, such as the pneumatic pressure sensor, the motor encoder (or other location determining mechanism), and any temperature sensors associated with the heater. The control unit is programmed to run all pumping sequences discussed herein, including the sequence discussed next.

In one pumping sequence, with an outlet valve (e.g., destination valve) closed and an inlet valve (e.g., source valve) open, the motor is caused to retract the piston within the cylinder, creating a negative pressure that pulls the flexible membrane into the rigid pump housing, towards the motor, causing the pump chamber to fill with any of the fluids discussed herein. The pneumatic pressure sensor provides feedback to the control unit, so that the negative pressure can be controlled to a desired level, e.g., for comfortably pumping effluent dialysis fluid from the patient. Other sources are not pressure restricted and can therefore be subject to higher negative pressures.

In a second step, with both inlet and outlet valves closed, the motor is caused to push the piston within the cylinder, creating a positive pressure $P_1$ and a volume of air between the membrane and the piston of $V_1$. No fluid is moved here. The pneumatic pressure sensor provides feedback to the control unit, so that the positive pressure in the next step can be controlled to a desired level, e.g., for comfortably pumping heated fresh dialysis fluid to the patient. Other destinations are not pressure restricted and can therefore be subject to higher positive pressures.

In a third step, the inlet valve is closed and the outlet valve is opened, allowing positive pressure built in the previous step to push fluid to the destination. Instead of letting the pressure fall from the starting pressure $P_1$ to a lowered pressure $P_2$, the system maintains the pumping pressure such that $P_2$ equals $P_1$ using a feedback algorithm. As soon as $P_2$ is sensed falling below $P_1$, the control unit causes the motor to push the piston further towards the pump chamber to build pressure within the sealed air chamber even though fluid is still being delivered to the destination. $P_2$ is repressurized so as to reach the higher positive pressure of $P_1$ as recorded by the control unit. The outlet valve is closed when a known and desired amount of fluid is delivered from the pump chamber. It has been found that at the end of a pump-out stroke, $P_2$ will likely not equal $P_1$ exactly. $P_2$ will be very close to $P_1$, but be off by a small fraction of a psig, for example. While the error is very small, it accumulates over multiple strokes (e.g., over forty strokes for a 50 ml stroke volume to reach a two liter fill or drain). The control unit at the end of each pump-out stroke accordingly makes a small adjustment of the piston to raise or lower the pressure slightly to match as exactly as possible a desired ending pressure for the pump-out stroke and a desired starting pressure for the subsequent pump-in stroke.

Since the repressurized $P_2$ pressure in the third step equals $P_1$ in the second step (assuming no thermal change), an air volume $V_2$ between the piston and the pump chamber in the third step equals an air volume $V_1$ between the piston and the pump chamber in the second step, which also means that the volume of fluid delivered between the second and third steps is equal to a volume change in piston positions between the second and third steps, which is accurately determined from the encoder or other position detection mechanism outputting to the control unit.

The system and method of the present disclosure uses the feedback algorithm to maintain the pressure constant over the pump-out stroke but does not do so for the pump-in stroke in one embodiment. Over multiple pump-in and pump-out strokes, time the aggregate amount of fluid pumped-out equals the amount of fluid removed from a source. Monitoring only the pump-out strokes is advantageous because it allows the pump-in strokes to be performed as quickly as possible to reduce the amount of time needed to fill the pump chamber. Pumping from a supply container or bag may be performed without regard to a patient pressure limit and thus may be performed at a higher pressure, e.g., negative five to seven psig. Doing so allows the pump chamber to be filled quickly. Pumping from the patient is performed according a patient limit, e.g., −1.5 psig, but nevertheless may be performed without having to ensure the negative pumping pressure is held constant throughout the pump-in stroke.

It should be appreciated that the effects of drift in the pneumatic pressure sensor are negated because the important aspect is that repressurized $P_2$ equals $P_1$ as described above, not that the pressures are accurate from an absolute standpoint. Also, because the system is pressure controlled, the linear actuator does not have to be accurate, rather, the positional detection of the piston needs to be accurate. Indeed an air pump or compressor could replace the motor as long as the position of the piston can be measured accurately.

In an optional embodiment, a vent is provided, for example, in the pneumatic line between the rigid pump housing and the cylinder, so that with both inlet and outlet valves closed after a delivery stroke, the piston can be moved all the way to the front cylinder wall illustrated with the vent open to relieve pressure. By doing so, the size, e.g., length, of the cylinder can be minimized.

It is contemplated to provide two pump chambers, two rigid pump housings, two sets of inlet and outlet valves, two piston-cylinders, two pneumatic lines each with pressure sensors (and possibly a vent), two motors with encoders or other position detection devices, two sets of fluid lines and two sets of valves operating with same. The sets are alternated such as one set is drawing fluid into its pump chamber, the other set is pumping the same or different fluid out of its pump chamber. In this manner fluid flow can be at least substantially continuous and increased.

In light of the disclosure set forth herein, and without limiting the disclosure in any way, in a first aspect of the present disclosure, which may be combined with any other aspect, a peritoneal dialysis system includes: a pump housing; a cylinder in pneumatic communication with the pump housing; a piston including a piston head slideably sealed within the cylinder; a linear actuator in mechanical communication with the piston; a pressure sensor positioned and arranged to sense a pressure within the pump housing caused by movement of the piston within the cylinder; a fluid inlet valve; a fluid outlet valve; a fluid pump chamber including a flexible membrane moved by the pressure within the pump housing when the fluid pump chamber is sealed to the pump housing; a fluid inlet line and a fluid outlet line in fluid communication with the fluid pump chamber; and a control unit configured to cause (i) the fluid inlet valve and the fluid outlet valve to occlude the fluid inlet line and the fluid outlet line, respectively, while the linear actuator moves the piston to create a positive pressure within the pump housing, the positive pressure measured by the pressure sensor, and (ii) the fluid inlet valve to occlude the fluid inlet line and the fluid outlet valve to open the fluid outlet line, while the linear actuator moves the piston so as to maintain the positive pressure within the pump housing while fluid is pumped out of the fluid pump chamber via the opened fluid outlet line.

In a second aspect of the present disclosure, which may be combined with any other aspect described herein, the control unit is further configured to cause, prior to (i), the fluid inlet valve to open the fluid inlet line and the fluid outlet valve to occlude the fluid outlet line, while the linear actuator moves the piston so as to create a negative pressure within the cylinder to pull fluid into the fluid pump chamber via the opened fluid inlet line.

In a third aspect of the present disclosure, which may be combined with any other aspect described herein, negative pressure is measured by the pressure sensor, the control unit operable with the pressure sensor and configured to stop the linear actuator when the negative pressure reaches a commanded pressure.

In a fourth aspect of the present disclosure, which may be combined with any other aspect described herein, the control unit is further configured to use a measured distance that the piston is moved during (ii) to perform a calculation of a volume of the fluid pumped out of the fluid pump chamber via the opened fluid outlet line.

In a fifth aspect of the present disclosure, which may be combined with any other aspect described herein, the calculation assumes the same positive pressure exists at the end of both (i) and (ii).

In a sixth aspect of the present disclosure, which may be combined with any other aspect described herein, calculation of volume includes at least one dimension of the cylinder.

In a seventh aspect of the present disclosure, which may be combined with any other aspect described herein, the linear actuator includes a position detection mechanism to provide the measured distance to the control unit.

In an eighth aspect of the present disclosure, which may be combined with any other aspect described herein, the control unit is further configured to add a plurality of the volumes of the fluid pumped out of the fluid pump chamber to determine a total volume of fluid pumped from the fluid pump chamber to a destination.

In a ninth aspect of the present disclosure, which may be combined with any other aspect described herein, the destination includes a patient catheter, a heating container or a drain location.

In a tenth aspect of the present disclosure, which may be combined with any other aspect described herein, the control unit is further configured to perform a pressure adjustment within the fluid pump chamber after (ii).

In an eleventh aspect of the present disclosure, which may be combined with any other aspect described herein, the source includes a patient catheter, a heating container or a fluid supply.

In a twelfth aspect of the present disclosure, which may be combined with any other aspect described herein, maintaining the positive pressure within the pump housing while fluid is pumped out of the fluid pump chamber includes (a) reestablishing the positive pressure after the positive pressure is initially lowered in (ii) or (b) holding the positive pressure at least substantially constant.

In a thirteenth aspect of the present disclosure, which may be combined with any other aspect described herein, the control unit is further configured to cause, during at least one of (i) or (ii), a second fluid inlet valve to open a second fluid inlet line and a second fluid outlet valve to occlude a second fluid outlet line, while a second linear actuator moves a second piston so as to create a negative pressure within a second cylinder to pull fluid into a second fluid pump chamber via the opened second fluid inlet line.

In a fourteenth aspect of the present disclosure, which may be combined with any other aspect described herein, at least one of (i) the inlet valve is a fluid supply line valve, a heater line valve or a patient line valve, or (ii) the outlet valve is the patient line valve, the heater line valve or a drain line valve.

In a fifteenth aspect of the present disclosure, which may be combined with any other aspect described herein, a peritoneal dialysis system comprises a cycler including a pump housing, a linear actuator, a pressure sensor positioned and arranged to sense a pressure within the pump housing caused by movement of the linear actuator, a fluid inlet valve, and a fluid outlet valve: a disposable set including a fluid pump chamber including a flexible membrane moved by the pressure within the pump housing when the fluid pump chamber is sealed to the pump housing, and a fluid inlet line and a fluid outlet line in fluid communication with the fluid pump chamber; and a control unit configured to cause (i) the fluid inlet valve and the fluid outlet valve to occlude the fluid inlet line and the fluid outlet line, respectively, while the linear actuator creates a positive pressure within the pump housing, the positive pressure measured by the pressure sensor, and (ii) the fluid inlet valve to occlude the fluid inlet line and the fluid outlet valve to open the fluid outlet line, while the linear actuator maintains the positive pressure within the pump housing and fluid is pumped out of the fluid pump chamber via the opened fluid outlet line.

In a sixteenth aspect of the present disclosure, which may be combined with any other aspect described herein, maintaining the positive pressure within the pump housing while fluid is pumped out of the fluid pump chamber includes (a) reestablishing the positive pressure after the positive pressure is initially lowered in (ii) or (b) holding the positive pressure at least substantially constant.

In a seventeenth aspect of the present disclosure, which may be combined with any other aspect described herein, the cycler further includes a cylinder in pneumatic communication with the pump housing, a piston including a piston head slideably sealed within the cylinder, the linear actuator in mechanical communication with the piston, and wherein the linear actuator moves the piston in (i) and (ii) to create and maintain the positive pressure.

In an eighteenth aspect of the present disclosure, which may be combined with any other aspect described herein, the linear actuator includes a motor in mechanical communication with a rotational to translational conversion apparatus.

In a nineteenth aspect of the present disclosure, which may be combined with any other aspect described herein, the fluid inlet valve and fluid outlet valve are pinch valves positioned and arranged to pinch or open the fluid inlet line and fluid outlet line, respectively.

In a twentieth aspect of the present disclosure, which may be combined with any other aspect described herein, the disposable set further includes at least one of a patient line, supply line, heater line or drain line in fluid communication with at least one of the fluid inlet line or fluid outlet line.

In a twenty-first aspect of the present disclosure, which may be combined with any other aspect described herein, the cycler further includes at least one of a patient line valve for allowing or occluding flow through the patient line, a supply line valve for allowing or occluding flow through the supply line, a heater line valve for allowing or occluding flow through the heater line, or a drain line valve for allowing or occluding flow through the drain line.

In a twenty-second aspect of the present disclosure, which may be combined with any other aspect described herein, at least one of (i) the fluid inlet line is a fluid supply line, a heater line or a patient line, or (ii) the fluid outlet line is the patient line, the heater line or a drain line.

In a twenty-third aspect, any of the features, functionality and alternatives described in connection with any one or more of FIGS. 1 to 9 may be combined with any of the features, functionality and alternatives described in connection with any other of FIGS. 1 to 9.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is a further advantage of the present disclosure to provide a relatively quiet APD cycler.

It is still another advantage of the present disclosure to provide an APD cycler that is accurate irrespective of drift in a pressure sensor with time, temperature, humidity, etc.

It is yet another advantage of the present disclosure to provide an APD cycler that removes a dependence of volumetric accuracy on absolute pressure sensing.

It is yet a further advantage of the present disclosure to provide an APD system that uses both a low cost and simple cycler and a low cost and simple disposable.

It is still a further advantage of the present disclosure to provide an APD system that is able to build motive fluid or pneumatic pressure in a relatively simple manner.

It is still another advantage of the present disclosure to provide an APD system that employs a relatively low cost disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
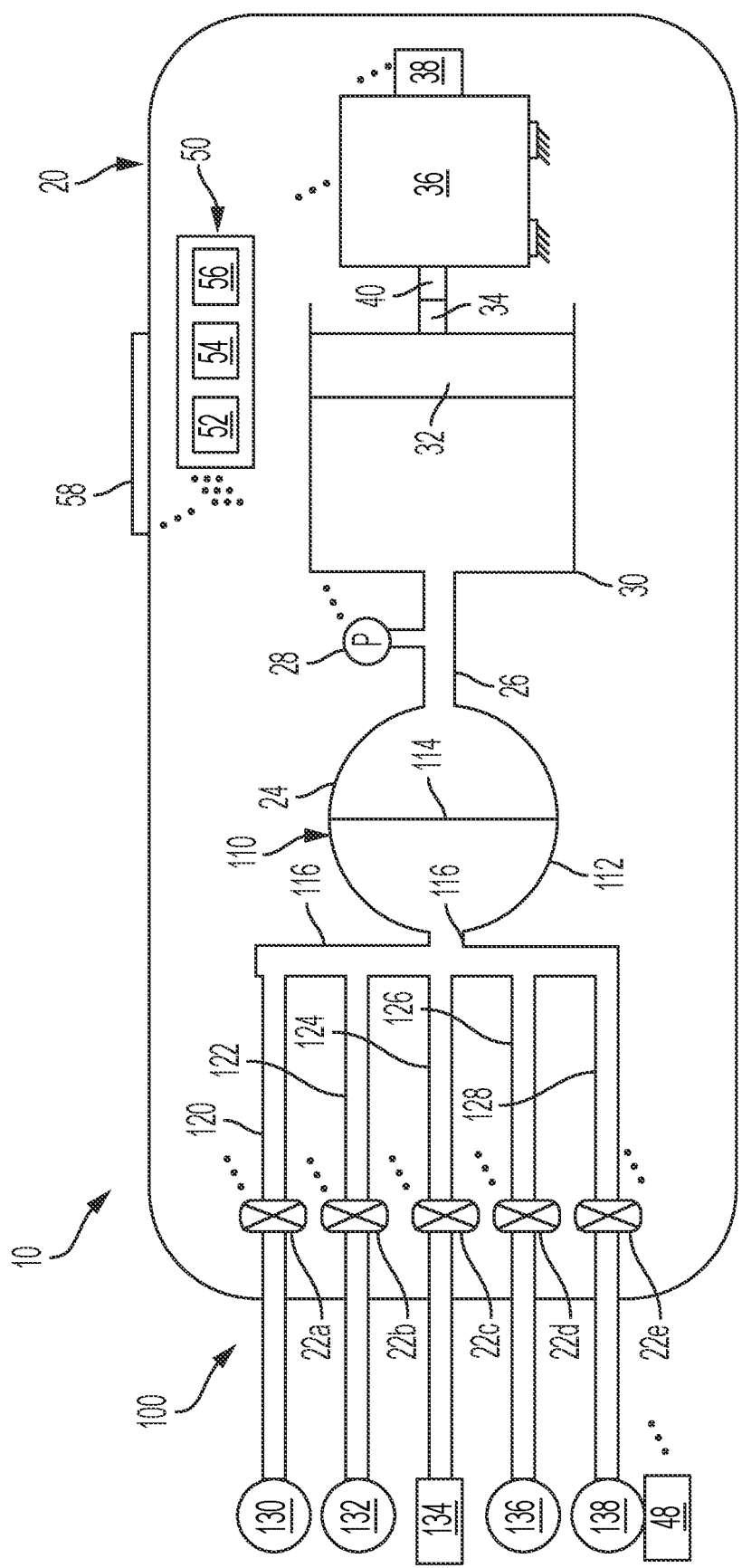
FIG. 1 is a top or side view illustrating one embodiment of a pressurized cylinder automated peritoneal dialysis ("APD") cycler of the present disclosure.

Referring now to the drawings and in particular to FIG. 1, an automated peritoneal dialysis ("APD") system 10 includes and APD machine or cycler 20 that operates with a disposable set 100. Disposable set 100 includes or defines a pump chamber 110, which in the illustrated embodiment includes a rigid, semi-spherical pump shell 112 to which a flexible membrane or diaphragm 114 is heat sealed, ultrasonically sealed, solvent bonded or otherwise welded. Rigid pump shell 112 may be made of plastic, such as, polyvinyl chloride ("PVC"), polyethylene ("PE"), polyurethane ("PU") or polycarbonate ("PC"). All flexible components of disposable set 100, such as membrane or diaphragm 114, the tubing and the containers discussed herein may be made of a medically safe material such as one or more plastic, e.g., PVC, PE, PU, or other suitable non-PVC polymer.

In the illustrated embodiment, a common inlet/outlet line 116 extends from pump chamber 110 and splits into multiple, e.g., five, separate lines. The separate lines may include at least one supply line 120 and a last fill line 122 to carry fresh dialysis fluid from supply and last fill containers 130 and 132, respectively, to pump chamber 110 before heating. Fresh dialysis fluid from supply or last fill containers 130 or 132 is then pumped from pump chamber 110 along a heater line 128 to a heating container 138 for batch heating. Heated, fresh dialysis fluid is then pumped from heating container 138 to pump chamber 110 via heater line 128. Heated, fresh dialysis fluid is then pumped from pump chamber 110 to the patient through a patient line 124 to a patient connector 134 that communicates fluidly with the patient's indwelling catheter via the patient's transfer set. After the fresh, heated dialysis fluid dwells within the patient for a prescribed amount of time, used dialysis fluid is then pumped from the patient through patient line 124 to pump chamber 110. Used dialysis fluid is finally pumped from pump chamber 110 through a drain line 126 to drain 136.

In an alternative embodiment, inline heating is provided that heats fresh dialysis fluid flowing through one or more of fresh dialysis fluid lines 120, 122 and/or patient line 124. In another alternative embodiment, fresh and last fill containers or bags 130, 132 are located within a heater chamber or blanket (not illustrated). It should also be appreciated that disposable set 100 may include supply lines 120 leading to multiple fresh dialysis fluid containers 130, which are each located within the heating blanket. In either alternative heating embodiment, a separate heater line and heating container or bag are not needed.

Figure 2:
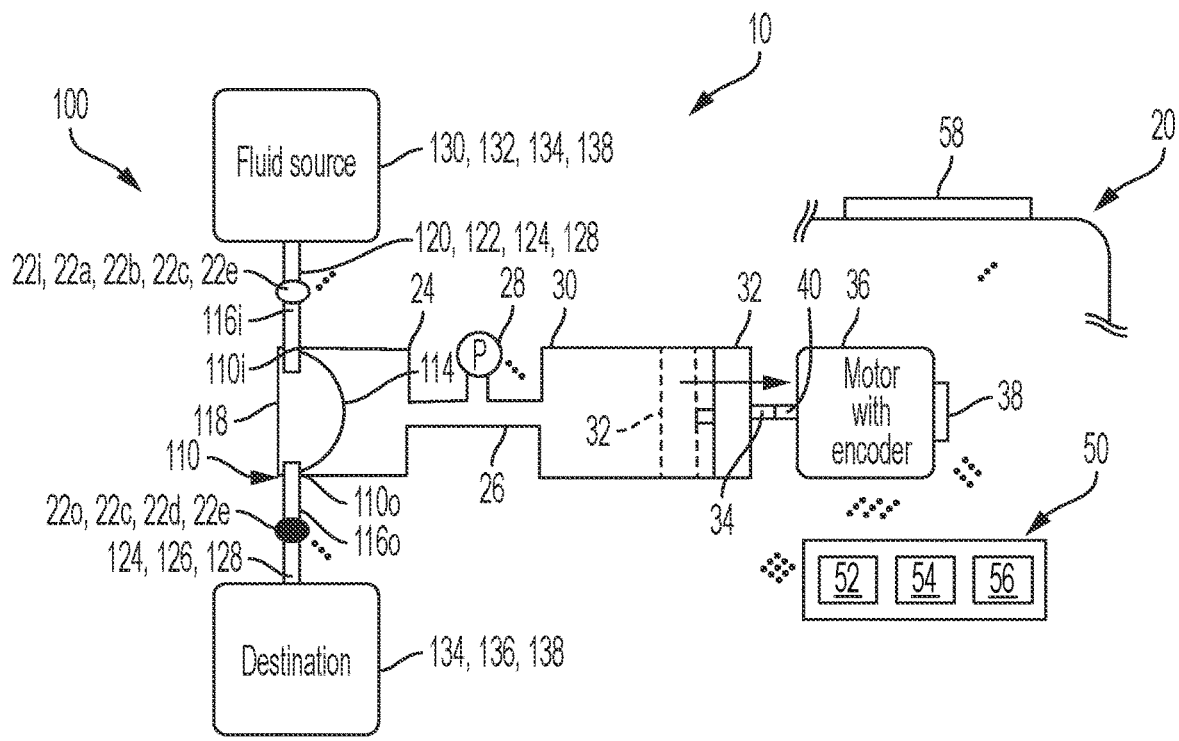
FIG. 2 is a top or side view illustrating another embodiment of a pressurized cylinder APD cycler of the present disclosure performing a first pumping sequence step.
Figure 3:
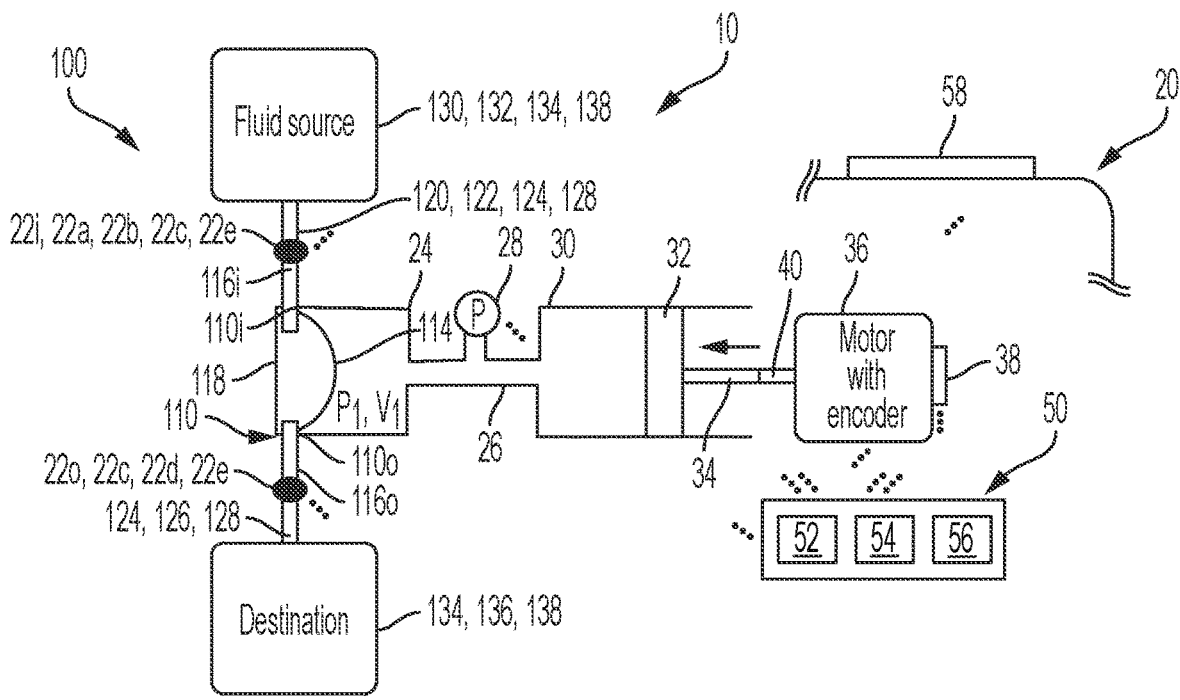
FIG. 3 is a top or side view illustrating the APD cycler of FIG. 2 performing a second pumping sequence step.
Figure 4:
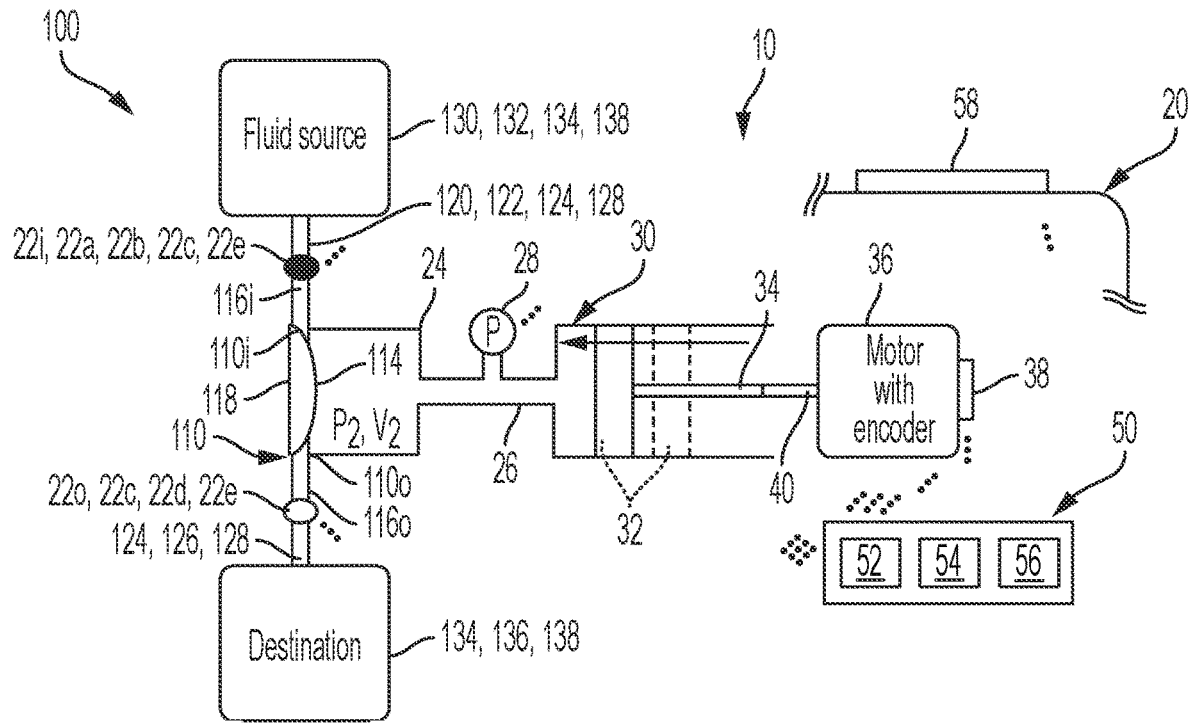
FIG. 4 is a top or side view illustrating the APD cycler of FIG. 2 performing a third pumping sequence step.

Flexible membrane 114 is in one embodiment circular and made of at least one ply or piece of flexible material. Flexible membrane 114 may be sealed (e.g., heat sealed, ultrasonically sealed, solvent bonded, or otherwise welded) to one half of rigid, semi-spherical pump shell 112, separating a fluid side of membrane 114 (left of membrane 114) from an air or pneumatic side of membrane 114 (right of membrane 114). FIGS. 2 to 4, 6 and 7 illustrate an alternative embodiment for pump chamber 110. Here, flexible membrane 114 is sealed (e.g., heat sealed, ultrasonically sealed, solvent bonded) to a disposable, cylindrical plate 118 instead of semi-spherical pump shell 112 in FIG. 1. FIGS. 2 to 4 also illustrate that common inlet/outlet line 116 of disposable set 100 may split into an inlet line 116i that runs to an inlet 110a of pump chamber 110 and an outlet line 116o that extends from an outlet 110b of the pump chamber. In a further alternative embodiment, diaphragm or membrane 114 may be welded to a second, like-shaped membrane.

As illustrated in FIGS. 1 to 4, 6, 7 and 9, cycler 20 in an embodiment provides a fluid valve 22a to 22e, such as an electrically actuated solenoid valve or a pneumatically actuated valve, for each fluid line listed above. In the illustrated embodiment, fluid valve 22a operates with supply line 120, fluid valve 22b operates with last fill line 122, fluid valve 22c operates with patient line 124, fluid valve 22d operates with drain line 126, while fluid valve 22e operates with heater line 128. Fluid valves 22a to 22e provide for independent control (open or closed) of each fluid line.

FIGS. 2 to 4, 6 and 7 illustrate that cycler 20 of system 10 also provides an inlet valve 22i that operates with an inlet line 116i extending to pump chamber 110 and an outlet valve 220 that operates with an outlet line 116o extending from pump chamber 110. The inlet and outlet valves 22i and 220 may also be electrically actuated solenoid valves or pneumatically actuated valves. It should be appreciated that inlet and outlet valves 22i and 220 may be separate from and additional to valves from fluid valves 22a to 22e or may at different times be one of fluid valves 22a to 22e. FIGS. 2 to 4, 6 and 7 accordingly illustrate that inlet valve 22i may be a separate valve or be any of supply container valve 22a, last fill container valve 22b, patient line valve 22c or heater valve 22e operating with supply line 120, last bag line 122, patient line 124 or heater line 128, respectively. FIGS. 2 to 4, 6 and 7 also illustrate that outlet valve 220 may be a separate valve or any of patient line valve 22c, drain line valve 22d or heater valve 22e operating with patient line 124, drain line 126 or heater line 128, respectively.

Figure 9:
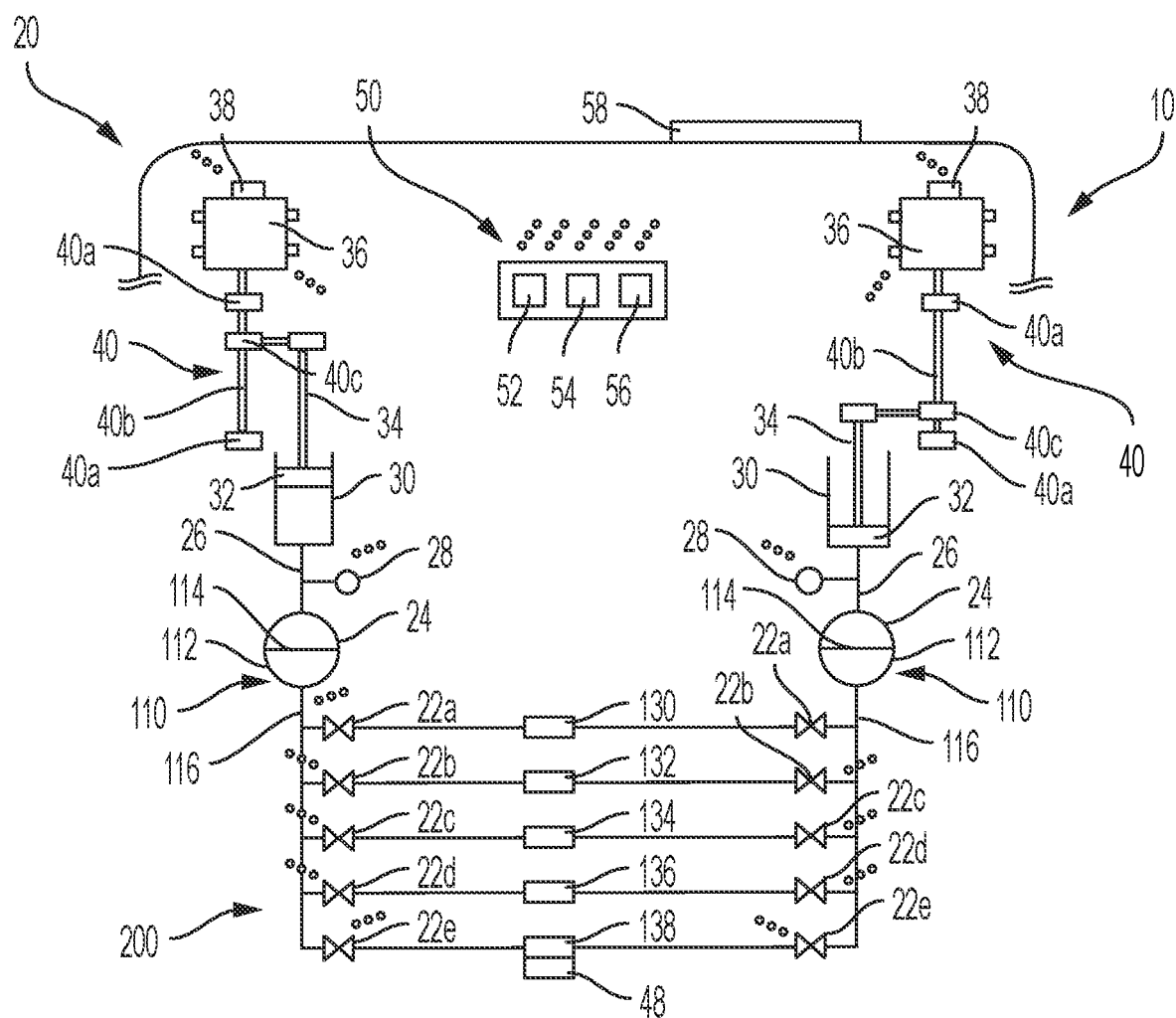
FIG. 9 is a top or side view illustrating still a further embodiment of a pressurized cylinder APD cycler of the present disclosure.

Also, while FIGS. 2 to 4, 6 and 7 illustrate separate inlet and outlet lines 116i and 116o, it should be appreciated that only a single line 116 leading into and out of pump chamber 100 is needed as illustrated in FIGS. 1 and 9. This is confirmed by the pumping sequences discussed in detail below in which only a single valve needs to be open at a given time in the pump sequence steps.

FIGS. 1 to 4 and 6, 7 and 9 illustrate that cycler 20 includes a rigid pump housing 24 that seals to and operates with the flexible pump chamber 100. Rigid pump housing 24 is in pneumatic communication with a cylinder 30 via a pneumatic pressure sensing line 26 having a pressure sensor 28. Rigid pump housing 24, pressure sensing line 26 and cylinder 30 are reusable in one embodiment and may be made of plastic, such as, polyvinyl chloride ("PVC"), polyethylene ("PE") or polyurethane ("PU"), or of metal, such as stainless steel or aluminum, and combinations thereof.

A piston 32 is moved back and forth within cylinder 30 via a piston shaft 34 coupled to a motor 36 operating with an encoder 38 (for knowing position of the piston). Piston 32 is slideably sealed to an inner wall of cylinder 30 as illustrated in FIGS. 1 to 4, 6, 7 and 9. Piston 32 and piston shaft 34 are in one embodiment mechanically coupled to and moved by a lead screw, ball screw of other rotational to translational conversion apparatus 40 to produce translational motion of piston 32 within cylinder 34 (detail in FIG. 9). A different type of linear actuator 40 and location determining mechanism may be used alternatively, such as a rack and pinion operated by motor 36, wherein the movement of the rack may be monitored by a potentiometer. Any of cylinder 30, piston 32, piston shaft 34 and any portion of linear actuator 40 may be reusable in one embodiment and may be made of plastic, such as, polyvinyl chloride ("PVC"), polyethylene ("PE") or polyurethane ("PU"), or of metal, such as stainless steel or aluminum, and combinations thereof.

FIGS. 1 and 9 illustrate that heating container or bag 138 is heated by a batch heater 48 in one embodiment. As mentioned above, the heater is alternatively an inline heater or thermal blanket. All valves 22a to 22e, 22i and 220, motor 36 (or other linear actuator 40), and fluid heater 48 are under control of a control unit 50, which includes at least one processor 52, at least one memory 54 and a video controller 56 for controlling a user interface 58 (which may be coupled to cycler 20 as illustrated or be a wireless user interface). Control unit 50 is also configured to receive signals from all sensors, such as the pneumatic pressure sensor 28, temperature sensors (not illustrated) associated with fluid heater 48, motor encoder 38 (or other location determining mechanism). Control unit 50 may also include a transceiver and a wired or wireless connection to a network, e.g., the internet, for sending treatment data to and receiving prescription instructions from a doctor's or clinician's server interfacing with a doctor's or clinician's computer. User interface 58 may include a display screen operating with a touchscreen and/or one or more electromechanical button, such as a membrane switch. User interface 58 may also include one or more speaker for outputting alarms, alerts and/or voice guidance commands.

Control unit 50 is programmed to run all pumping sequences discussed herein, including the sequences discussed next. As illustrated in FIG. 2, in a first step of one pumping sequence, with the outlet valve 220, 22c, 22d or 22e closed and the inlet valve 22i, 22a, 22b, 22c or 22e open, motor 36 operating as part of linear actuator 40 is caused to retract piston 32 within cylinder 30, creating a negative pressure that pulls flexible membrane 114 into rigid pump housing 24, towards motor 36, causing pump chamber 110 to fill with any of the fluids discussed herein. Pneumatic pressure sensor 28 provides feedback to control unit 50, so that the negative pressure can be controlled to a desired level, e.g., up to −3 psig, for comfortably pumping effluent dialysis fluid from the patient.

As illustrated in FIG. 3, in a second step of the pumping sequence, with both inlet valve 22i, 22a, 22b, 22c or 22e and outlet valve 220, 22c, 22d or 22e closed, motor 36 operating as part of linear actuator 40 is caused to push piston 32 within cylinder 30, creating a positive pressure $P_1$ and a volume of air between membrane 114 and piston 32 of $V_1$. No fluid is moved here. Pneumatic pressure sensor 28 provides feedback to control unit 50 so that the positive pressure in the next step can be controlled to a desired level, e.g., up to +3 to 5 psig, for comfortably pumping heated fresh dialysis fluid to the patient.

As illustrated in FIG. 4, in a third step, inlet valve 22i, 22a, 22b, 22c or 22e is closed and outlet valve 220, 22c, 22d or 22e is opened, allowing positive pressure built in the previous step to push fluid to any desired destination 134, 136, 138. Instead of letting the pressure fall from the starting pressure $P_1$ (FIG. 3) to a lowered pressure $P_2$ (FIG. 4), system 10 maintains the pumping pressure such that $P_2$ equals $P_1$ using a feedback algorithm, e.g., the algorithm of FIG. 5. As soon as $P_2$ is sensed falling below $P_1$ (it is possible that $P_2$ initially falls below $P_1$), control unit 50 causes motor 36 as part of linear actuator 40 to push piston 32 further towards the pump chamber 110 to build pressure within the sealed rigid pump housing 24 even though fluid is still being delivered to a destination 134, 136, 138. Pressure $P_2$ is repressurized so as to reach the higher positive pressure of $P_1$ as recorded by control unit 50. Control unit 50 closes outlet valve 220, 22c, 22d or 22e when a known and desired amount or volume of fluid is delivered from pump chamber 110.

It has been found that at the end of a pump-out stroke, pressure $P_2$ (FIG. 4) will likely not equal pressure $P_1$ (FIG. 3) exactly. $P_2$ will be very close to $P_1$, but be off by a small fraction of a psig, for example. While the error is very small, it accumulates over multiple strokes (e.g., over forty strokes for a 50 ml stroke volume to reach a two liter fill or drain). In one embodiment, control unit 50 at the end of each pump-out stroke accordingly actuates motor 36 operating as part of linear actuator 40 to make a small adjustment of piston 32 within cylinder 30 to raise or lower the pressure slightly, while outlet valve 220, 22c, 22d or 22e is closed, to match $P_2$ as exactly as possible to $P_1$ prior to a subsequent pump-in stroke.

Since the repressurized $P_2$ pressure in the third step (FIG. 4) equals $P_1$ in the second step (FIG. 3, assuming no thermal change), air volume $V_2$ between piston 32 and pump chamber 110 in the third step equals air volume $V_1$ between piston 32 and pump chamber 110 in the second step, which also means that the volume of fluid delivered between the second step (FIG. 3) and third step (FIG. 4) is equal to the volume change the position of piston 32 between the second and third steps, which is determined from encoder 38 or other position detection mechanism of linear actuator 40 outputting to control unit 50 multiplied by the inner diameter cross-sectional area of cylinder 30, which is stored in memory 54 of control unit 50.

System 10 and associated methodology of the present disclosure uses a feedback algorithm (e.g., algorithm of FIG. 5) for control unit 50 to maintain pumping pressure so as to be as constant as possible over a pump-out stroke but does not do so for a pump-in stroke in one embodiment. Over multiple pump-in and pump-out strokes, time the aggregate amount of fluid pumped-out equals the amount of fluid removed from a source. Monitoring only the pump-out strokes is advantageous because it allows the pump-in strokes to be performed as quickly as possible to reduce the amount of time needed to fill pump chamber 110. Pumping from a supply or heating container or bag 130, 132, 138 may be performed without regard to a patient pressure limit and thus may be performed at a higher pressure, e.g., negative five to seven psig. Doing so allows the pump chamber 110 to be filled quickly. Pumping from patient 134 is performed according a patient limit, e.g., −1.5 psig, but nevertheless may be performed without having to ensure the negative pumping pressure is held constant throughout the pump-in stroke.

Figure 5:
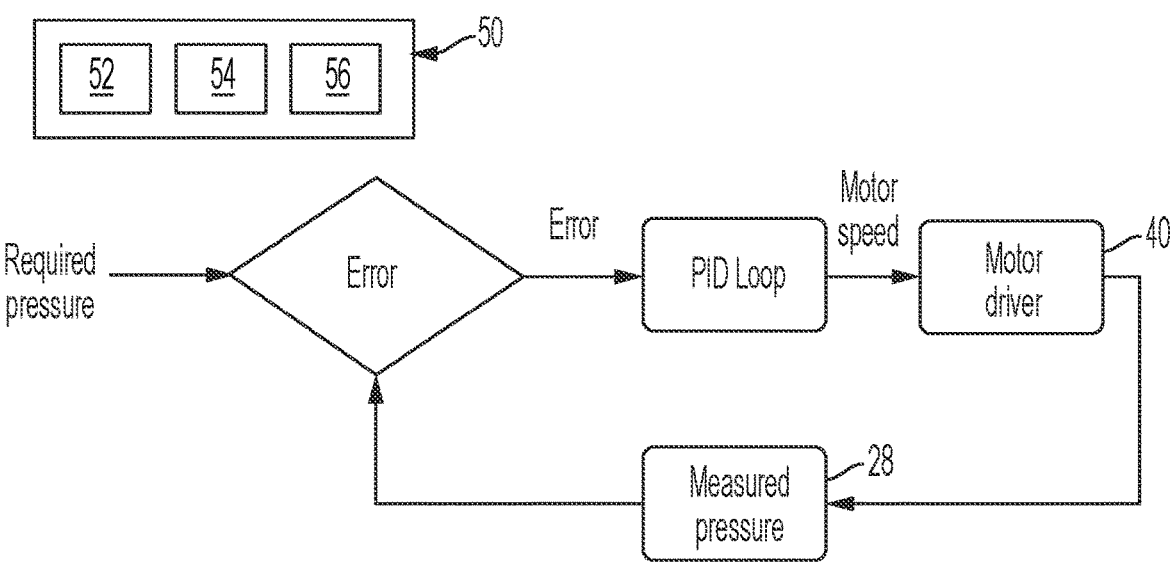
FIG. 5 is a schematic diagram illustrating one embodiment of a pressure feedback loop used with the pressure sensor in the sequence of FIGS. 2 to 4.

FIG. 5 illustrates that processing 52 and memory 54 of control unit 50 uses the pressure signal from pressure sensor 28 as feedback to vary the speed of the linear actuator 40 (may be a separate card of control unit 50), e.g., for motor 36, to make sure that the resulting positive or negative fluid pressure does not exceed an allowable limit. The pressure limits may be different for different fluid sources and destinations. In FIG. 5, control unit 50 sets a pressure to be achieved (not just avoiding a pressure limit), which is compared against a pressure signal measured by pressure sensor 28. The difference may be fed into a control algorithm, e.g., a proportional, integral, differential ("PID") algorithm, which attempts to reduce the difference between the commanded pressure and the measured pressure to zero, and results in an output to the electronic motor driver in one example of linear actuator 40. The above analysis is performed on some periodic frequency in each of the different steps of system 10 described in FIGS. 2 to 4.

Figure 6:
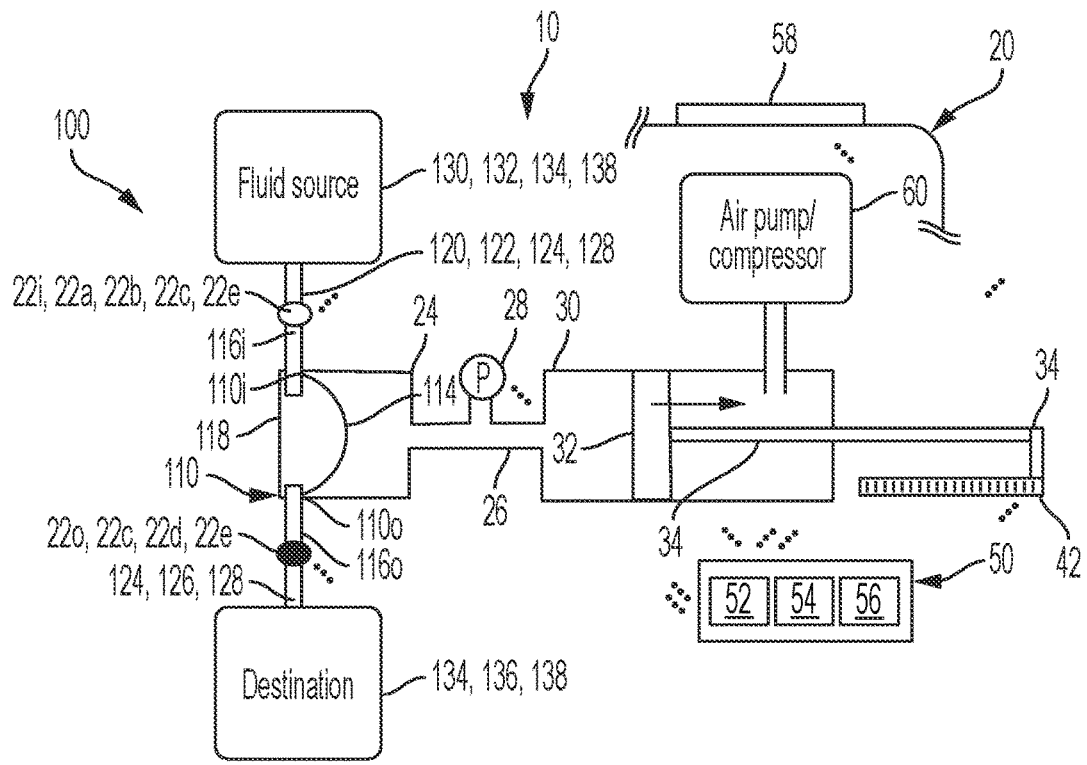
FIG. 6 is a top or side view illustrating still another embodiment of a pressurized cylinder APD cycler of the present disclosure.

It should be appreciated that the effects of drift in pressure sensor 28 are negated because the important aspect is that repressurized $P_2$ equals $P_1$ as described above, not that the pressures are accurate from an absolute standpoint. Also, because system 10 is pressure controlled, linear actuator 40 does not have to be able to move itself accurately, rather, the positional detection of piston 32, e.g., via encoder 38, potentiometer (not illustrated), etc., needs to be accurate. Indeed, FIG. 6 illustrates an alternative embodiment in which an air pump or compressor 60 replaces motor 32. Here, a potentiometer 42 of linear actuator 40, connected directly or indirectly to piston shaft 34, outputs accurate piston position information to control unit 50 so that the above procedure of FIGS. 2 to 4 may be performed.

Figure 7:
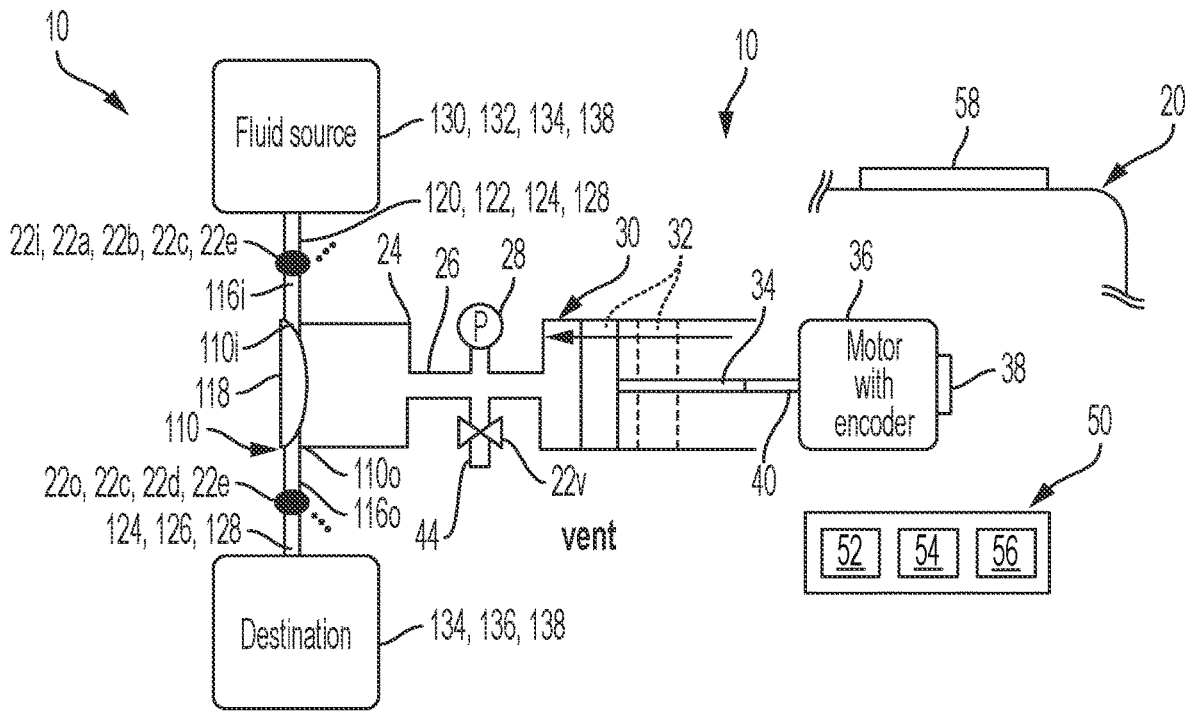
FIG. 7 is a top or side view illustrating yet another embodiment of a pressurized cylinder APD cycler of the present disclosure.

FIG. 7 illustrates an alternative embodiment for system 10 in which cycler 20 provides a vent 44 opened and closed by a vent valve 22v, which is under control of control unit 50. Vent 44 is placed in pneumatic communication with pneumatic line 26 located between rigid pump housing 24 and cylinder 30 in the illustrated embodiment of FIG. 7. Control unit 50 is programmed in connection with FIG. 7 so that with both inlet valve 22i, 22a, 22b, 22c or 22e and outlet valve 220, 22c, 22d or 22e closed after a delivery stroke, linear actuator 40 can move piston 32 all the way to a front cylinder wall 30f with vent valve 22v open to relieve pressure within rigid pump housing 24 and cylinder 30 prior to commencement of the next sequence set forth in FIGS. 2 to 4. By doing so, the size, e.g., length, of cylinder 30 may be minimized. Cylinder 30 and pump chamber 110 may be sized to allow for a pump-out volume per stroke to be, e.g., fifty to one-hundred milliliters.

Figure 8:
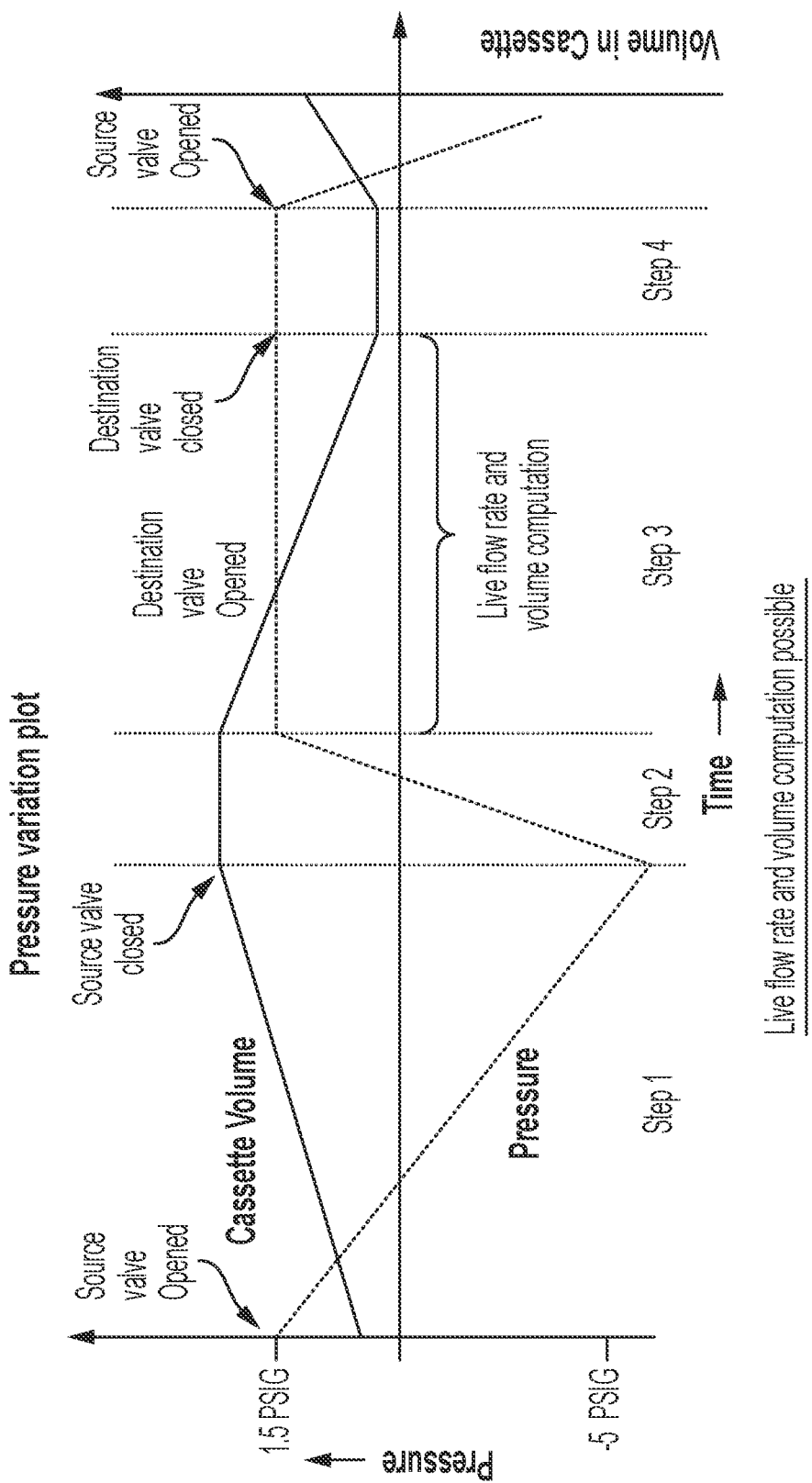
FIG. 8 is a graph illustrating an example patient fill stroke using any of the pressurized cylinder APD cycler embodiments described herein.

Referring now to FIG. 8, a graph illustrating an example patient fill stroke using any of the pressurized cylinder APD cycler embodiments described herein is illustrated. The patient drain stroke operates the same as the patient fill stroke except that the negative pump-in pressure for the patient drain is regulated to a limit, e.g., −1.5 psig. In the illustrated patient fill stroke, negative pressure to the heating container 138 can be appreciably higher, e.g., −5.0 psig in step 1 of the fill stroke. In step 1, the pressure begins at the positive ending pressure of the previous stroke, e.g., +1.5 psig, while the volume in pump chamber 110 is low. Over step 1, control unit 50 causes motor 36 to retract piston 32 within cylinder 30 with the inlet valve open, so that negative pressure is increased to a maximum pump-in value, here −5.0 psig, filling pump chamber 110 to a level that is equal to or higher than the desired pump-out volume. Over step 2, control unit 50 causes motor 36 to advance piston 32 within cylinder 30 with the inlet and outlet valves closed, so that positive pressure is built to a desired pump-out pressure, here +1.5 psig. The volume of fresh dialysis fluid within pump chamber 110 does not change over step 2. Over step 3, control unit 50 causes motor 36 to advance piston 32 within cylinder 30 with the outlet valve open to pump a desired volume of fresh dialysis fluid to the patient. Here, the pressure sensor feedback algorithm, e.g., of FIG. 5, is employed so that the positive pressure remains constant, e.g., at +1.5 psig, over the step 3. The volume of fluid within pump chamber 110 decreases by the prescribed fill volume in step 3. Step 4 involves the adjustment of piston 32 within cylinder 30 by control unit 50 to raise or lower the pressure slightly, while outlet valve 220, 22c, 22d or 22e is closed, to match as exactly as possible a desired ending pressure, here +1.5 psig, for the pump-out stroke and a desired starting pressure for the subsequent pump-in stroke. For example, control unit 50 in step 4 may adjust piston 32 so that the pressure increases from +1.48 psig to +1.50 psig (or from +1.52 psig to +1.50 psig). While the pressure appears to be constant in step 4, it is varied slightly as discussed. The end of step 4 places system 10 back to the conditions at the beginning of step 1.

Referring now to FIG. 9, system 10 in an alternative embodiment includes a cycler 20 having a pair of linear actuators 40 under control of control unit 50 and a pair of cylinders 30. In particular, system 10 of FIG. 9 includes a pair of linear actuators, each including a motor 36 having an encoder 38. Linear actuators 40 in the illustrated embodiment also include bearings 40a holding a lead or ball screw 40b. Lead or ball screws 40b drive translating fixtures 40c, which are connected to piston shafts 34 that move pistons 32 as discussed above in FIGS. 2 to 4. Pistons 32 are located within cylinders 30 and are moved to create the negative and positive pressures discussed above. Cylinders 30 are connected pneumatically to rigid pump housings 24 via pneumatic lines 26 having pressure sensors 28. Rigid pump housings 24 are sealed for operation to pump chambers 110.

Pump chambers 110 each include a semi-spherical pump shell 112 that holds a flexible membrane or diaphragm 114. Pump chambers 110 are part of alternative disposable set 200. Alternative disposable set 200 incudes a pair of inlet/outlet lines 116 that lead to two sets of supply lines, last fill lines, patient lines, drain lines and heater lines. The supply lines both lead to at least one fresh dialysis fluid supply container 130. The last fill lines both lead to last fill container 132. The patient lines both lead to patient connector 134. The drain lines both lead to drain container 136. The heater lines both lead to heating container 138.

System 10 of FIG. 9 allows one linear actuator 40 to cause fluid to be pumped-out, while the other linear actuator 40 causes fluid, e.g., the same fluid, to be pumped-in. The two sets of supply lines, last fill lines, patient lines, drain lines and heater lines are under the respective control, via control unit 50, of supply line valves 22a, last fill line valves 22b, patient line valves 22c, drain line valves 22d and heater valves 22e. Control unit 50 therefore allows, in a first pump sequence, any fluid to be pumped into one of pump chambers 110, while any other fluid is pumped out of the other pump chamber 110. In a second pump sequence, control unit 50 changes the roles of the two pump chambers 110. System 10 of FIG. 9 accordingly allows for more continuous flow and for a higher, e.g., doubled, flowrate.

In various examples, system 10 of FIG. 9 under control of control unit 50 in a first pump sequence enables fresh dialysis fluid (pre-last fill or last fill) to be pulled into one of pump chambers 110, e.g., at any suitable pressure because pulling from dialysis fluid container 130 or 132 does not require a pressure limit, while fresh dialysis fluid is pushed from the other pump chamber 110, e.g., at any suitable pressure because pushing dialysis fluid to heating container 138 does not require a pressure limit. Next, the roles of the two pump chambers 110 are reversed. Control unit 50 in an embodiment repeats the first pump sequence until either dialysis fluid container 130 is empty or heating container 138 is full.

In another example, system 10 of FIG. 9 under control of control unit 50 in a second pump sequence enables heated dialysis fluid to be pulled into one of pump chambers 110, e.g., at any suitable pressure because pulling from heating container 138 does not require a pressure limit, while heated, fresh dialysis fluid is pushed from the other pump chamber 110, e.g., at +3 to 5 psig, because pushing dialysis fluid to the patient does involve a pressure limit. Next, the roles of the two pump chambers 110 are reversed. Control unit 50 in an embodiment repeats the second pump sequence until either heating container 138 is empty or the patient's prescribed fill volume has been delivered to the patient.

In a further example, system 10 of FIG. 9 under control of control unit 50 in a third pump sequence enables used dialysis fluid or effluent to be pulled into one of pump chambers 110, e.g., at −3 psig because pulling used or effluent fluid from the patient does involve a pressure limit, while used dialysis fluid or effluent is pushed from the other pump chamber 110, e.g., at any suitable pressure because pushing used fluid to drain 136 (container or house drain) does not require a pressure limit. Next, the roles of the two pump chambers 110 are reversed. Control unit 50 in an embodiment repeats the third pump sequence until the patient is empty, e.g., according to a prescribed patient drain or to a drain algorithm.

It should be understood that various changes and modifications to the presently preferred embodiments described herein will be apparent to those skilled in the art. For example, while valves 22 (collectively referring to all valves are illustrated as being tubing pinch valves, valves 22 may alternatively be cassette-based valves, such as pneumatic volcano valves. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis system comprising:
 a pump housing;
 a cylinder in pneumatic communication with the pump housing;
 a piston including a piston head slidably sealed within the cylinder;
 a linear actuator in mechanical communication with the piston;
 a pressure sensor positioned and arranged to sense a pressure within the pump housing caused by movement of the piston within the cylinder;
 a fluid inlet valve;
 a fluid outlet valve;
 a fluid pump chamber including a flexible membrane moved by the pressure within the pump housing when the fluid pump chamber is sealed to the pump housing;
 a fluid inlet line and a fluid outlet line in fluid communication with the fluid pump chamber; and
 a control unit configured to cause (i) the fluid inlet valve and the fluid outlet valve to occlude the fluid inlet line and the fluid outlet line, respectively, while the linear actuator moves the piston to create a positive pressure within the pump housing, the positive pressure measured by the pressure sensor, and (ii) the fluid inlet valve to occlude the fluid inlet line and the fluid outlet valve to open the fluid outlet line, while the linear actuator moves the piston so as to maintain the positive pressure within the pump housing while fluid is pumped out of the fluid pump chamber via the opened fluid outlet line.

2. The peritoneal dialysis system of claim 1, wherein the control unit is further configured to cause, prior to (i), the fluid inlet valve to open the fluid inlet line and the fluid outlet valve to occlude the fluid outlet line, while the linear actuator moves the piston so as to create a negative pressure within the cylinder to pull fluid into the fluid pump chamber via the opened fluid inlet line.

3. The peritoneal dialysis system of claim 2, wherein the negative pressure is measured by the pressure sensor, the control unit operable with the pressure sensor and configured to stop the linear actuator when the negative pressure reaches a commanded pressure.

4. The peritoneal dialysis system of claim 1, wherein the control unit is further configured to use a measured distance that the piston is moved during (ii) to perform a calculation of a volume of the fluid pumped out of the fluid pump chamber via the opened fluid outlet line.

5. The peritoneal dialysis system of claim 4, wherein the calculation assumes the same positive pressure exists at the end of both (i) and (ii).

6. The peritoneal dialysis system of claim 4, wherein the calculation of the volume includes at least one dimension of the cylinder.

7. The peritoneal dialysis system of claim 4, wherein the linear actuator includes a position detection mechanism to provide the measured distance to the control unit.

8. The peritoneal dialysis system of claim 4, wherein the control unit is further configured to add a plurality of the volumes of the fluid pumped out of the fluid pump chamber to determine a total volume of fluid pumped from the fluid pump chamber to a destination.

9. The peritoneal dialysis system of claim 8, wherein the destination includes a patient catheter, a heating container or a drain location.

10. The peritoneal dialysis system of claim 8, wherein the control unit is further configured to perform a pressure adjustment within the fluid pump chamber after (ii).

11. The peritoneal dialysis system of claim 8, wherein the source includes a patient catheter, a heating container or a fluid supply.

12. The peritoneal dialysis system of claim 1, wherein maintaining the positive pressure within the pump housing while fluid is pumped out of the fluid pump chamber includes (a) reestablishing the positive pressure after the positive pressure is initially lowered in (ii) or (b) holding the positive pressure at least substantially constant.

13. The peritoneal dialysis system of claim 1, wherein the control unit is further configured to cause, during at least one of (i) or (ii), a second fluid inlet valve to open a second fluid inlet line and a second fluid outlet valve to occlude a second fluid outlet line, while a second linear actuator moves a second piston so as to create a negative pressure within a second cylinder to pull fluid into a second fluid pump chamber via the opened second fluid inlet line.

14. The peritoneal dialysis system of claim 1, wherein at least one of (i) the inlet valve is a fluid supply line valve, a heater line valve or a patient line valve, or (ii) the outlet valve is the patient line valve, the heater line valve or a drain line valve.

15. A peritoneal dialysis system comprising:
a cycler including
  a pump housing,
  a linear actuator,
  a pressure sensor positioned and arranged to sense a pressure within the pump housing caused by movement of the linear actuator,
  a fluid inlet valve, and
  a fluid outlet valve:
a disposable set including
  a fluid pump chamber including a flexible membrane moved by the pressure within the pump housing when the fluid pump chamber is sealed to the pump housing, and
  a fluid inlet line and a fluid outlet line in fluid communication with the fluid pump chamber; and
a control unit configured to cause (i) the fluid inlet valve and the fluid outlet valve to occlude the fluid inlet line and the fluid outlet line, respectively, while the linear actuator creates a positive pressure within the pump housing, the positive pressure measured by the pressure sensor, and (ii) the fluid inlet valve to occlude the fluid inlet line and the fluid outlet valve to open the fluid outlet line, while the linear actuator maintains the positive pressure within the pump housing and fluid is pumped out of the fluid pump chamber via the opened fluid outlet line.

16. The peritoneal dialysis system of claim 15, wherein maintaining the positive pressure within the pump housing while fluid is pumped out of the fluid pump chamber includes (a) reestablishing the positive pressure after the positive pressure is initially lowered in (ii) or (b) holding the positive pressure at least substantially constant.

17. The peritoneal dialysis system of claim 15, wherein the cycler further includes a cylinder in pneumatic communication with the pump housing, a piston including a piston head slidably sealed within the cylinder, the linear actuator in mechanical communication with the piston, and wherein the linear actuator moves the piston in (i) and (ii) to create and maintain the positive pressure.

18. The peritoneal dialysis system of claim 15, wherein the linear actuator includes a motor in mechanical communication with a rotational to translational conversion apparatus.

19. The peritoneal dialysis system of claim 15, wherein the fluid inlet valve and fluid outlet valve are pinch valves positioned and arranged to pinch or open the fluid inlet line and fluid outlet line, respectively.

20. The peritoneal dialysis system of claim 15, wherein the disposable set further includes at least one of a patient line, supply line, heater line or drain line in fluid communication with at least one of the fluid inlet line or fluid outlet line.

21. The peritoneal dialysis system of claim 20, wherein the cycler further includes at least one of a patient line valve for allowing or occluding flow through the patient line, a supply line valve for allowing or occluding flow through the supply line, a heater line valve for allowing or occluding flow through the heater line, or a drain line valve for allowing or occluding flow through the drain line.

22. The peritoneal dialysis system of claim 20, wherein at least one of (i) the fluid inlet line is a fluid supply line, a heater line or a patient line, or (ii) the fluid outlet line is the patient line, the heater line or a drain line.

* * * * *